(12) United States Patent
Aldrett-Lee et al.

(10) Patent No.: US 7,906,679 B2
(45) Date of Patent: Mar. 15, 2011

(54) METAL SURFACES TO INHIBIT ETHYLENICALLY UNSATURATED MONOMER POLYMERIZATION

(75) Inventors: Salvador Aldrett-Lee, Katy, TX (US); Diane E. Allen, St. Charles, MO (US); Olan Stanley Fruchey, Hurricane, WV (US); Roger L. Roundy, Hurricane, WV (US); Tao Wang, Houston, TX (US)

(73) Assignee: Arkema Inc., Philadelphia, PA (US)

( * ) Notice: Subject to any disclaimer, the term of this patent is extended or adjusted under 35 U.S.C. 154(b) by 1160 days.

(21) Appl. No.: 10/571,797

(22) PCT Filed: Sep. 24, 2003

(86) PCT No.: PCT/US03/30076
§ 371 (c)(1),
(2), (4) Date: Jul. 19, 2006

(87) PCT Pub. No.: WO2005/040084
PCT Pub. Date: May 6, 2005

(65) Prior Publication Data
US 2008/0228002 A1    Sep. 18, 2008

(51) Int. Cl.
*C07C 51/16* (2006.01)
*B01J 19/00* (2006.01)
(52) U.S. Cl. ........................................ 562/545; 422/240
(58) Field of Classification Search ............... 562/542, 562/545, 546; 422/240
See application file for complete search history.

(56) References Cited

U.S. PATENT DOCUMENTS

| 5,922,912 | A | 7/1999 | Kambara et al. |
| 6,441,228 | B2 * | 8/2002 | Nakahara et al. ............. 562/600 |
| 2002/0165407 | A1 | 11/2002 | Nakahara et al. |
| 2004/0030179 | A1 | 2/2004 | Martin et al. |

OTHER PUBLICATIONS

Ullmann's Encyclopedia of Industrial Chemistry, 5$^{th}$ Edition, vol. A1, pp. 166-167, W. Gerhartz et al., 1985-1996, ISBN 3-527-20100-9.

* cited by examiner

*Primary Examiner* — Nizal S Chandrakumar
(74) *Attorney, Agent, or Firm* — Steven D. Boyd

(57) ABSTRACT

Materials for making apparatus and a method of inhibiting polymerization during manufacture, purification, handling and storage of subject ethylenically unsaturated monomers are disclosed. In particular, copper or metals containing copper, in the presence of oxygen, have inhibit undesired polymerization resulting in polymer fouling in apparatus used during the manufacture, purification, handling and storage of the monomers, such as acrylic acid, methacrylic acid, acrylic acid esters and methacrylic acid esters. The copper or copper alloys as described herein, in the presence of an oxygen-containing gas, exhibit self-inhibiting surface characteristics when used to make at least a portion of the apparatus to inhibit polymerization of the monomers in contact with the portion of the apparatus including such copper-containing metal.

15 Claims, 1 Drawing Sheet

METAL SURFACES TO INHIBIT ETHYLENICALLY UNSATURATED MONOMER POLYMERIZATION

CROSS REFERENCE TO RELATED APPLICATIONS

This application is a 371 of PCT/US03/30076 filed Sep. 24, 2003.

BACKGROUND OF THE INVENTION

This invention is directed to polymerization inhibition during the manufacture, purification, handling or storage of ethylenically unsaturated monomers.

Normally, during production, including manufacture and purification, as well as during handling and storage of ethylenically unsaturated monomers, there is a need to add polymerization inhibitors such as hydroquinone (HQ), mono methyl ether of hydroquinone (MEHQ), phenothiazine (PTZ), hindered amine radical trap compounds, or a catechol, such as tertiary butyl catechol or di-tertiary butyl catechol. Additional exemplary inhibitors generally employed include phenolic compounds characterized by the presence of at least one other substituent on the benzene ring. Such other substituent serves to activate the phenolic inhibitor. Representative substituents include a $C_1$-$C_4$ alkoxy group such as methoxy or ethoxy, hydroxyl, sulfhydryl, amino, a $C_1$-$C_9$ alkyl group, phenyl, nitro, or N-linked amide, for example.

It is well known that in the absence of inhibitors, unintended polymerization, resulting in polymer fouling, can readily occur and not only impact production handling or storage of the desired product, but also result in equipment failure. Further, additional energy is required to operate the production units, such as distillation equipment, for example. Purification, particularly involving distillation equipment, is of great concern, since this equipment requires a large amount of energy to operate and operates at high temperatures. The increased temperatures increase the likelihood of polymerization occurring.

The majority of the inhibitors employed are contained in the liquid monomers. The surfaces of the equipment not in contact with the liquid containing the inhibitor provide open sites for polymerization or fouling. An example is any portion of equipment where vapors undergo condensation, since the condensate would no longer contain the inhibitors in the original monomer liquid. Hence, there is a need for protection of the equipment surfaces, which are typically metal surfaces, exposed to such monomers, as well as the monomers themselves, so as to inhibit polymer formation during manufacture, purification, handling or storage of an ethylenically unsaturated monomer.

U.S. Pat. No. 6,441,228 B2 and U.S. patent application Publication No. US 2002/0165407 A1, published Nov. 7, 2002; both of Nakahara et al., disclose a method and apparatus for producing (meth)acrylic acid, wherein the apparatus contains molybdenum so as to minimize corrosion and pitting of the surface, which in turn minimizes polymerization of the (meth)acrylic acid and associated fouling of the equipment by polymerized products. The Nakahara et al. documents disclose using for the production apparatus a metal made of a nickel chromium iron alloy having a molybdenum content of greater than 3% to 20% or a molybdenum content of 1 to 4% with 0.5% to 7% copper.

The present invention satisfies the need in the industry to inhibit polymerization of ethylenically unsaturated monomers during their manufacture, purification, handling or storage by the use of novel materials for at least a portion of the apparatus in which the monomers are in contact.

BRIEF SUMMARY OF THE INVENTION

One aspect of the present invention relates to an apparatus for at least one of manufacture, purification, handling and storage of a subject ethylenically unsaturated monomer, the apparatus comprising an inlet for an oxygen-containing gas, and at least a portion of the apparatus in contact with the monomer comprising a metal containing sufficient copper to inhibit, in the presence of the oxygen-containing gas, polymerization of the monomer within the apparatus.

Another aspect of the present invention relates to a method for inhibiting polymerization during at least one of manufacture, purification, handling and storage of a subject ethylenically unsaturated monomer, the method comprising the steps of:

introducing the monomer into apparatus for at least one of the manufacture, purification, handling and storage of the monomer, at least a portion of the apparatus in contact with the monomer comprising a metal containing sufficient copper to inhibit, in the presence of a gas containing oxygen, polymerization of the monomer within the apparatus; and providing a gas containing oxygen in the interior of the apparatus containing the monomer;

thereby inhibiting polymerization of the monomer in the apparatus.

As used herein, the article "a" or "an" or a reference to a singular subject includes the plural or more than one subject, unless specifically and explicitly restricted to the singular or a single subject, or unless otherwise clear from the context containing the term.

As used herein, "about," with respect to any numerical value, means a variation from the stated value by an amount that would not materially affect the characteristics of the product or process to which the value relates.

As used herein, "inhibit" or word forms thereof, means to reduce the likelihood, reduce or minimize, and preferably, prevent the occurrence of an event, such as polymerization.

As used herein, "percent" or "%" of a component means percent by weight of a component within an alloy, substance or composition containing the component.

As used herein, the term "subject ethylenically unsaturated monomer" means any polymerizable ethylenically unsaturated monomer that has an unsubstituted or substituted carboxylic acid or ester group, other than methyl acrylate or 2-ethylhexyl acrylate.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

Figure 1:
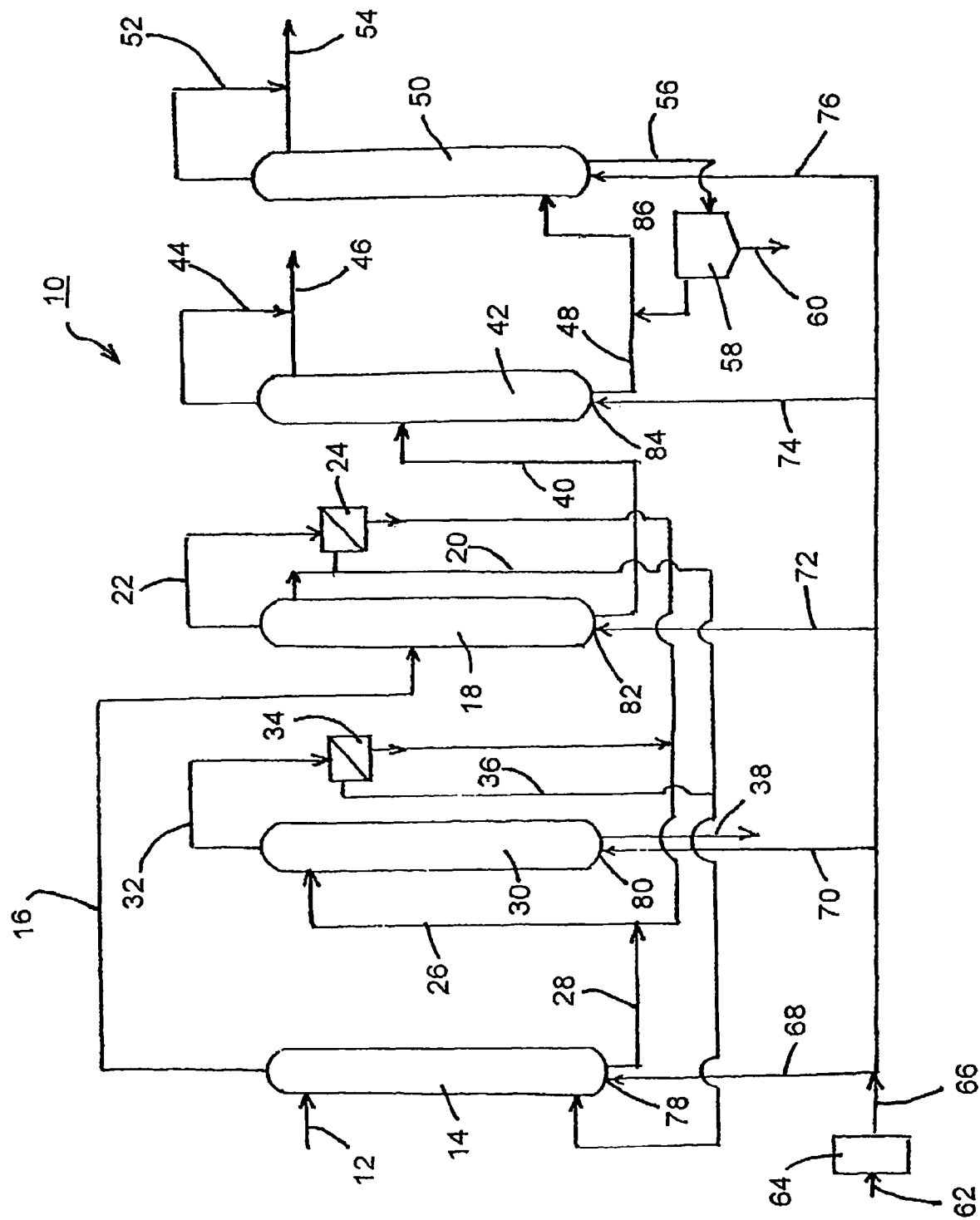

The sole FIGURE is a schematic diagram of an exemplary acrylic acid recovery and purification apparatus made using components according to the present invention.

DETAILED DESCRIPTION OF THE INVENTION

The present invention involves the use of materials for construction of at least a portion of a polymerization-resistant apparatus associated with the manufacture, purification, handling or storage of a subject ethylenically unsaturated monomer to inhibit the polymerization of such monomer on surfaces of the apparatus. In particular, copper or metals containing at least about 10% copper, are employed in the construction of such apparatus. It appears that the higher the copper content of the metal used in the apparatus, the better it acts to inhibit polymerization and thereby prevent polymer fouling in equipment, such as distillation towers, used during the manufacture, purification, handling or storage of the subject ethylenically unsaturated monomers. Unlike the references of Nakahara et al., the present invention does not involve a mechanism associated with minimizing pitting or corrosion of the surface of the apparatus in contact with the monomers. Nor is molybdenum content considered a necessary metal component for polymerization inhibition in the present invention.

The present invention also concerns the method for inhibiting polymerization during manufacture, purification, handling or storage of the subject ethylenically unsaturated monomers by using copper-containing metal in at least a portion of the apparatus, in the presence of an oxygen-containing gas, used for any of the foregoing purposes. The method to inhibit polymerization or fouling is believed to involve a migration or leaching of copper ions from the copper metal or alloy present in at least a portion of the apparatus in contact with the subject ethylenically unsaturated monomer, which occurs in the presence of the oxygen-containing gas. It is believed that the copper ions that migrated from the metal provide the polymerization inhibition.

Although the invention is discussed primarily with respect to purification equipment, such as distillation equipment, it is also useful in other types of equipment where polymerization is a concern, such as flame arrestors. Specific non-limiting examples of apparatus and components for the production of the subject ethylenically unsaturated monomers include the reactors, distillation towers, distillation columns, any distillation internal components, absorbers, adsorbers, reboilers, condensers, distributors (liquid and vapor), extraction towers and ancillary equipment or components, such as heat exchangers, packing or trays for any of the components, piping, fittings, valving, pumps, or containers, including tanks and vessels that are part of the apparatus. The apparatus or any of its parts or components may be part of a system or separate items and may be stationary, mobile or portable equipment. By way of further example without limitation, in the case of distillation trays, the entire tray does not have to be made from the copper-containing metal. If blanking strips are used, then they alone can be made from the copper-containing metal. If a distillation tower is employed, the inside surface may be only somewhat covered with the copper-containing metal. It is possible to fabricate a distillation tower with partial internal covering of the copper-containing metal, which will be sufficient to provide the desired polymerization inhibition.

Likewise, although the invention is discussed primarily with respect to production of acrylic acid, it is useful in connection with the manufacture, purification, handling or storage of any other of the subject ethylenically unsaturated monomers, such as, for example without limitation other than as mentioned above, an alpha alkyl acrylic acid, an alpha alkyl acrylic ester, a beta alkyl acrylic acid, a beta alkyl acrylic ester, methacrylic acid, an ester of acrylic acid other than methyl acrylate and 2-ethylhexyl acrylate, an ester of methacrylic acid, vinyl acetate, a vinyl ester, a polyunsaturated carboxylic acid, a polyunsaturated ester, maleic acid, a maleic ester, maleic anhydride, and acetoxystyrene. The alkyl group for any of the foregoing compounds is preferably a straight chain or branched alkyl group having 1 to 8 carbon atoms, and more preferably, a straight chain or branched alkyl group having 1 to 4 carbon atoms.

The use of copper or copper-containing metal according to the present invention inhibits the polymerization reactions that occur with respect to the subject ethylenically unsaturated monomers, when the monomers are in contact with the metal used in the apparatus of the present invention.

The present invention does not eliminate the need for the use with the monomers of conventional in-process polymerization inhibitors, such as hydroquinone (HQ), mono methyl ether of hydroquinone (MEHQ), phenothiazine (PTZ), hindered amine radical trap compounds, or a catechol, such as tertiary butyl catechol or di-tertiary butyl catechol, or other typical polymerization inhibitors, for instance phenolic compounds characterized by the presence of at least one other substituent on the benzene ring. Such other substituent serves to activate the phenolic inhibitor. Representative substituents include a $C_1$-$C_4$ alkoxy group such as methoxy or ethoxy, hydroxyl, sulfhydryl, amino, a $C_1$-$C_9$ alkyl group, phenyl, nitro, or N-linked amide, for example.

The material of construction for the apparatus containing or used for the manufacture, purification, handling and storage of ethylenically unsaturated monomers is copper or a metal containing at least about 10% copper. It has been found that this metal exhibits self-inhibiting surface characteristics for the apparatus or parts thereof made from such metal.

Preferred metals include not only metals that are about 100% copper, but also alloys containing at least about 10% copper. The metals preferably have a composition comprising about 25% to about 75% copper, and more preferably about 30% to about 50% copper. Preferred alloys include bronze (comprising about 90% to about 99% copper and about 1% to about 10% tin); brass (an alloy comprising primarily copper and zinc), in several varieties, such as red brass (about 85% copper and about 15% zinc), yellow brass (about 63% to about 66% copper and about 34% to about 37% zinc), cartridge brass (about 67% to about 70% copper and about 30% to about 33% zinc), admiralty brass, sometimes called admiralty metal (about 67% to about 70% copper, about 25.8% to about 29.25% zinc and about 0.75% to about 1.2% tin), and Munz metal (about 60% copper and about 40% zinc); and copper-niclcel alloys, for instance those available as Monel® alloys from Special Metals Corporation, Huntington, W.V. The Monel® alloys are particularly preferred, for instance Monel® alloys 400, 401, 404, R-405 and K-500, due to their strength relative to structural support, ability to be easily welded, ability to withstand temperatures generally up to about 538° C. (about 1,000° F.), and relatively low cost.

The indicated Monel® alloys have the following compositions, according to information available from Special Metals Corporation:

TABLE 1

| Limiting Chemical Composition, %, of Monel ® Alloy 400 | |
|---|---|
| Nickel (plus Cobalt) | 63.0 min. |
| Carbon | 0.3 max. |
| Manganese | 2.0 max. |
| Iron | 2.5 max. |
| Sulfur | 0.024 max. |
| Silicon | 0.5 max. |
| Copper | 28.0-34.0 |

TABLE 2

Limiting Chemical Composition, %, of Monel ® Alloy 401

| | |
|---|---|
| Nickel | 40.0-45.0 |
| Carbon | 0.10 max. |
| Manganese | 2.25 max. |
| Iron | 0.75 max. |
| Cobalt | 0.25 max. |
| Sulfur | 0.015 max. |
| Silicon | 0.25 max. |
| Copper | Bal. |

TABLE 3

Limiting Chemical Composition, %, of Monel ® Alloy 404

| | |
|---|---|
| Nickel (plus Cobalt) | 52.0-57.0 |
| Carbon | 0.15 max. |
| Manganese | 0.10 max. |
| Iron | 0.50 max. |
| Sulfur | 0.024 max. |
| Silicon | 0.10 max |
| Copper | Bal. |
| Aluminum | 0.05 max. |

TABLE 4

Limiting Chemical Composition, %, of Monel ® Alloy R-405

| | |
|---|---|
| Nickel (plus Cobalt) | 63.0 min. |
| Carbon | 0.3 max. |
| Manganese | 2.0 max. |
| Iron | 2.5 max. |
| Sulfur | 0.025-0.060 |
| Silicon | 0.5 max. |
| Copper | 28.0-34.0 |

TABLE 5

Limiting Chemical Composition, %, of Monel ® Alloy K-500

| | |
|---|---|
| Nickel (plus Cobalt) | 63.0 min. |
| Carbon | 0.25 max. |
| Manganese | 1.5 max. |
| Iron | 2.0 max. |
| Sulfur | 0.01 max. |
| Silicon | 0.5 max. |
| Copper | 27.0-33.0 |
| Aluminum | 2.30-3.15 |
| Titanium | 0.35-0.85 |

The polymerization inhibition must take place in the presence of an oxygen-containing gas, which may be substantially pure oxygen or other oxygen-containing gas (e.g. at least about 5 volume % oxygen), most conveniently air. The air or other oxygen-containing gas may be introduced into the equipment components of the apparatus, preferably though any suitable inlet and preferably a valved inlet, located at a lower portion of the equipment, and more preferably from the bottom, so that the oxygen-containing gas can be present throughout the apparatus wherever any undesired polymerization may occur.

While not wishing to be bound by any theory, it is believed that oxygen enhances the migration of copper ions from the copper-containing metal by the subject ethylenically unsaturated monomer. Thus, it is believed that the oxygen in the air or other oxygen-containing gas promotes the entry of copper ions into the liquid monomer. The inhibition effect of copper is believed to be based on the following chemistry. Above room temperature, or at elevated temperatures, in the presence of an ethylenically unsaturated monomer having a carboxylic acid or ester functionality and oxygen, very small amounts (on the order of a few parts per million) of copper metal in the copper-containing metal will be oxidized to cupric ion ($Cu^{+2}$), which then dissolves in the monomer that may be present, for example, as a condensed liquid. It is believed that this cupric ion plays a key role in the inhibition process. In the course of polymerization of the monomer, carbon centered free radicals are present during chain propagation. The cupric ion undergoes a one-electron transfer from the carbon-centered free radical yielding cuprous ion ($Cu^{+1}$) and a carbocation ($R^+$) (see Equation 1):

$$Cu^{+2} + R^* \rightarrow Cu^{+1} + R^+ \qquad \text{Equation 1:}$$

By removing the free radical, chain propagation (i.e. polymerization) stops. The cuprous ion is then oxidized by oxygen from the oxygen-containing gas back to cupric ion, which can then remove another carbon-centered radical from solution. In this manner, the copper is catalytic as long as oxygen is present in the system. If oxygen is not present, it is believed that the copper will slowly plate-out (i.e., coat onto the metal surface) as a result of the following reaction (Equation 2):

$$Cu^{+1} + Cu^{+1} \rightarrow Cu^\circ + Cu^{+2} \qquad \text{Equation 2:}$$

The apparatus and method of the present invention provide polymerization protection for condensed liquids on surfaces in metal equipment such as distillation columns, which generally do not have process inhibitors (e.g. PTZ or HQ) uniformly present due to poor distribution of the liquids in the equipment.

The invention will now be described with reference to the sole drawing FIGURE which was adapted from *Ullmann's Encyclopedia of Industrial Chemistry*, 5th Edition, Vol. A1, pp. 166-167, the disclosure of which is hereby incorporated herein by reference. The apparatus shown in the FIGURE is used only for purposes of explanation and is not intended to limit the application of the present invention in any way. The drawing is a schematic diagram of an acrylic acid recovery and purification apparatus 10 using a light extraction solvent, in which at least some of the components are made using copper or a metal containing at least about 10% copper according to the present invention.

In the apparatus 10, an acrylic acid-water mixture obtained from a production facility (not shown) is supplied for recovery and purification of acrylic acid through an inlet line 12 to an extraction column 14. The aqueous acrylic acid is introduced countercurrent to a light organic solvent with a boiling point lower than acrylic acid, such as ethyl acetate, butyl acetate, ethyl acrylate and 2-butanone, or any mixture thereof, for example. The solvent must have a high distribution coefficient for acrylic acid and a low solubility in water, and it must form an azeotrope containing a high percentage of water.

The extract from the top of the extraction column 14 passes through a line 16 into a solvent-separation column 18, where the solvent and water are distilled overhead in a line 22, condensed and separated in a condenser/separator 24, and the solvent is recycled through a line 20 back to the extraction column 14. Water from the overhead condenser/separator 24 passes through a line 26. The bottom stream from the extraction column 14 passes through a line 28 and into the line 26, where the bottom stream from the extraction column 14 and water from the solvent-separation column 18 are sent to a raffinate-stripping column 30. A small amount of solvent is recovered from the raffinate-stripping column 30 by distillation after passing through a line 32, a condenser/separator 34 and a line 36 into the recycle line 20 and back into the extraction column 14. Wastewater from the raffinate-stripping column 30 is drawn off through a line 38 and biologically treated or incinerated.

The bottom fraction from the solvent-separation column 18 is fed through a line 40 into a light-ends cut column 42, where acetic acid is distilled off through a line 44, condensed and, if desired, sent through a line 46 for recovery. Crude acrylic acid from the bottom of the light-ends cut column 42 is sent through a line 48 to a product column 50, where acrylic acid of high purity is obtained overhead through a line 52, condensed and sent for storage or distribution through a line 54. The material from the bottom of the product column 50 containing acrylic acid and acrylic acid dimer is fed through a line 56 to a decomposition evaporator 58, where the dimer is decomposed to the monomer. The evaporator residue, comprising acrylic acid oligomers, polymers and inhibitors, is withdrawn through a line 60 and sent for recovery of components, incinerated or otherwise appropriately disposed.

Because acrylic acid is readily polymerized, the distillation columns are operated with an inhibitor as described above, in the presence of oxygen, and at reduced pressure to lower the distillation temperature. The purity of acrylic acid produced by this process usually exceeds 99.5% and the purified yield is typically about 98%.

An oxygen-containing gas, preferably air, although substantially pure oxygen from any suitable source can be used if desired, is directed through an inlet line 62 into a compressor 64. From the compressor 64, air or other oxygen-containing gas is distributed through lines 66, 68, 70, 72, 74 and 76, respectively into the extraction column 14 through an inlet 78, into the raffinate-stripping column 30 through an inlet 80, into the solvent-separation column 16 through an inlet 82, into the light-ends cut column 42 through an inlet 84 and into the product column 50 through an inlet 86. The inlets into the various columns are located in a lower portion of the columns, and preferably the bottom of the lower portion of the columns or reboiler inlets so that the oxygen may be present throughout the columns and the lines leading from the columns.

At least a portion of the inner surface of the columns, or their inner components, as well as the fittings, lines, piping, valves (not shown for sake of clarity), pumps (not shown for sake of clarity), and other components should be made at least partially and preferably substantially entirely of copper or a metal containing at least about 10% copper, and preferably a Monel® alloy, according to the present invention. By using the metal of the present invention in an apparatus for manufacturing, purifying, handling or storing a subject ethylenically unsaturated monomer, polymerization of the monomer is inhibited, even in portions where the liquid monomer containing any pre-dissolved inhibitors cannot reach.

The invention will now be described in more detail with reference to the following specific, non-limiting examples:

SPECIFIC EMBODIMENTS OF THE INVENTION

EXAMPLE 1

Twelve 10 mL DOT (Department of Transportation) tubes were filled with 5 mL of glacial acrylic acid containing about 200 ppm of MeHQ inhibitor. Three tubes were used as the control and different metal chips were placed in the other nine tubes. Three tubes contained about 0.1 g of 316 stainless steel chips, three tubes contained about 0.1 g Monel® alloy chips and three tubes contained about 0.1 g of copper chips. The twelve tubes were open and placed in a hot oil bath at about 110° C. (about 230° F.). The tubes were agitated at regular intervals and allowed to mix with air. The tubes were inspected periodically for polymer formation. The results of the test are contained in the following Table 6, wherein the data represent an average of the three respective experiments:

TABLE 6

Results of Induction Time* Tests

| Treatment | Control | Stainless Steel | Copper | Monel® |
|---|---|---|---|---|
| Acrylic Acid (mL) | 5 | 5 | 5 | 5 |
| Average Run Time Without Polymerization (hrs) | 5 | 6 | >970 | >970 |
| Comments | Formed polymer | Formed Polymer | No Polymer | No Polymer |

*Induction Time means the amount of time it takes for the onset of polymerization.

EXAMPLE 2

The copper and Monel® alloy test of Example 1 was repeated using glacial acrylic acid which did not contain any MeHQ inhibitor. The experiment was stopped after 17 days (about 400 hrs) with no signs of polymer in any of the DOT tubes containing Monel® alloy or copper.

EXAMPLE 3

A three neck 250 mL glass round bottom flask was fitted with a 30.5 cm (12 inch) long glass tube filled with Monel® alloy packing material (about 35 g and about 6.1 mm (about 0.24 inch long from Cannon Instrument Company). Glacial acrylic acid (about 200 g containing about 500 ppm PTZ) was placed in the round bottom flask and the flask then fitted with a thermowell probe for monitoring temperature, and an air bleed. A distillation head was attached to the top of the Monel® alloy packed column. The contents of the flask were heated with an oil bath and stirred magnetically. The distillate was collected in 10 mL portions and then recycled to the flask. The overhead temperature during the run was about 147° C. (about 297° F.). The run lasted about 70 minutes during which time no polymer formed on the packing. Significant amounts of polymer were observed on the glass of the distillation head above the top of the Monel® alloy packing. The residue of acrylic acid in the pot had a light blue color and a copper content of about 52 ppm, determined by atomic absorption.

Example 3 was not reproduced with stainless steel as a surface, as it was clear that polymerization or fouling would have occurred promptly.

The data and results of the foregoing examples indicate that the copper and Monel® alloy served as enhanced polymerization inhibitor surfaces as compared to glass or stainless steel surfaces. It can be seen that the reaction within glass or on the stainless steel surface fouled within 5-6 hours, while the copper and Monel® alloy prevented polymerization up to greater than 970 hours (greater than 40 days).

While some copper leached out into the product during the experiments conducted, it is anticipated that the copper would not be a concern during a full purification run. This is due to the product going through additional distillation processes to remove heavy end impurities, which will also remove any remaining copper metal present. The copper and copper alloy metal are not volatile, and therefore would be anticipated to combine with the heavy end impurities.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for inhibiting polymerization during at least one of manufacture, purification, handling and storage of a subject ethylenically unsaturated monomer, the method comprising the steps of:

introducing the monomer into apparatus for at least one of the manufacture, purification, handling and storage of the monomer, at least a portion of the apparatus in contact with the ethylenically unsaturated monomer selected from the group consisting of acrylic acid, an alpha alkyl acrylic acid, an alpha alkyl acrylic ester, a beta alkyl acrylic acid, a beta alkyl acrylic ester, methacrylic acid, an ester of acrylic acid other than methyl acrylate and 2-ethylhecyl acrylate, an ester of methacrylic acid, vinyl acetate, a vinyl acetate, a vinyl ester, a polyunsaturated carboxylic acid, a polyunsaturated ester, maleic acid, a maleic ester, maleic anhydride, and acetoxystyrene comprising a metal alloy containing sufficient copper to inhibit, in the presence of a gas containing oxygen, polymerization of the monomer within the apparatus, wherein said metal alloy comprises more than 40% nickel and cobalt, 25% to less than 60% copper and not more than 2.5% iron; and providing a gas containing oxygen in the interior of the apparatus containing the monomer;

thereby inhibiting polymerization of the monomer in the apparatus.

2. The method of claim 1, wherein the alkyl group is a straight chain or branched alkyl group having 1 to 8 carbon atoms.

3. The method of claim 2, wherein the alkyl group is a straight or branched alkyl group having 1 to 4 carbon atoms.

4. The method of claim 1 wherein the ethylenically unsaturated monomer is acrylic acid.

5. The method of claim 1 wherein the ethylenically unsaturated monomer is ethyl acrylate.

6. The method of claim 1 wherein the ethylenically unsaturated monomer is butyl acrylate.

7. The method of claim 1, wherein the metal alloy contains about 30% to about 50% copper.

8. The method of claim 1 wherein the apparatus is selected from the group consisting of distillation equipment, a distillation internal component, flame arrestor equipment, extraction tower equipment, absorption equipment, adsorption equipment, heat exchange equipment, piping, a fitting, valving, a pump and a container.

9. The method of claim 1, wherein the apparatus is distillation equipment and the portion of the apparatus is packing.

10. The method of claim 1, wherein the apparatus is a distillation column.

11. The method of claim 10, wherein the oxygen-containing gas is provided through an inlet for the oxygen-containing gas at a lower portion of the distillation column.

12. The method of claim 1, wherein the apparatus is a distillation column and the portion comprises trays for the distillation column.

13. The method of claim 1, wherein the oxygen-containing gas is provided through an inlet for the oxygen-containing gas at a lower portion of the apparatus.

14. The method of claim 1, wherein the oxygen-containing gas is air.

15. The method of claim 1, wherein the oxygen-containing gas contains about 5 volume % oxygen.

* * * * *